US009173898B2

(12) United States Patent
Zheng et al.

(10) Patent No.: US 9,173,898 B2
(45) Date of Patent: Nov. 3, 2015

(54) METHODS OF TREATING GIARDIASIS (75) Inventors: Wei Zheng, Potomac, MD (US);
Catherine Chen, Germantown, MD (US); Juan Jose Marugan, Gaithersburg, MD (US); Noel Southall, Potomac, MD (US); Christopher P. Austin, Potomac, MD (US); Andrey Galkin, Germantown, MD (US); Liudmila Kulakova, Germantown, MD (US); Osnat Herzberg, Rockville, MD (US)

(73) Assignees: THE UNITED STATES OF AMERICA, as represented by the Secretary, Department of Health and Human Services, Bethesda, MD (US); University of Maryland, College Park, College Park, MD (US)

( * ) Notice: Subject to any disclaimer, the term of this patent is extended or adjusted under 35 U.S.C. 154(b) by 256 days.

(21) Appl. No.: 13/878,832

(22) PCT Filed: Oct. 12, 2011

(86) PCT No.: PCT/US2011/055902
§ 371 (c)(1),
(2), (4) Date: Jun. 13, 2013

(87) PCT Pub. No.: WO2012/051251
PCT Pub. Date: Apr. 19, 2012

(65) Prior Publication Data
US 2014/0148398 A1 May 29, 2014

Related U.S. Application Data (60) Provisional application No. 61/392,096, filed on Oct. 12, 2010, provisional application No. 61/411,509, filed on Nov. 9, 2010.

(51) Int. Cl.
| *A01N 43/04* | (2006.01) |
| *A61K 31/70* | (2006.01) |
| *A61K 31/7135* | (2006.01) |
| *A61K 31/05* | (2006.01) |
| *A61K 31/137* | (2006.01) |
| *A61K 31/145* | (2006.01) |
| *A61K 31/167* | (2006.01) |
| *A61K 31/28* | (2006.01) |
| *A61K 31/285* | (2006.01) |
| *A61K 31/336* | (2006.01) |
| *A61K 31/345* | (2006.01) |
| *A61K 31/351* | (2006.01) |
| *A61K 31/396* | (2006.01) |
| *A61K 31/4184* | (2006.01) |
| *A61K 31/42* | (2006.01) |
| *A61K 31/427* | (2006.01) |
| *A61K 31/428* | (2006.01) |
| *A61K 31/436* | (2006.01) |
| *A61K 31/475* | (2006.01) |
| *A61K 31/498* | (2006.01) |
| *A61K 31/4995* | (2006.01) |
| *A61K 31/525* | (2006.01) |
| *A61K 31/69* | (2006.01) |
| *A61K 31/704* | (2006.01) |
| *A61K 31/7068* | (2006.01) |
| *A61K 31/714* | (2006.01) |
| *A61K 31/426* | (2006.01) |
| *A61K 31/4375* | (2006.01) |
| *A61K 31/706* | (2006.01) |

(52) U.S. Cl.
CPC ............ *A61K 31/7135* (2013.01); *A61K 31/05* (2013.01); *A61K 31/137* (2013.01); *A61K 31/145* (2013.01); *A61K 31/167* (2013.01); *A61K 31/28* (2013.01); *A61K 31/285* (2013.01); *A61K 31/336* (2013.01); *A61K 31/345* (2013.01); *A61K 31/351* (2013.01); *A61K 31/396* (2013.01); *A61K 31/4184* (2013.01); *A61K 31/42* (2013.01); *A61K 31/426* (2013.01); *A61K 31/427* (2013.01); *A61K 31/428* (2013.01); *A61K 31/436* (2013.01); *A61K 31/4375* (2013.01); *A61K 31/475* (2013.01); *A61K 31/498* (2013.01); *A61K 31/4995* (2013.01); *A61K 31/525* (2013.01); *A61K 31/69* (2013.01); *A61K 31/704* (2013.01); *A61K 31/706* (2013.01); *A61K 31/7068* (2013.01); *A61K 31/714* (2013.01)

(58) Field of Classification Search
CPC .................................................. A61K 31/7135
USPC ....................................................... 514/23, 24
See application file for complete search history.

(56) References Cited

U.S. PATENT DOCUMENTS

2010/0273762 A1  10/2010 Burke et al.

OTHER PUBLICATIONS

Vint, I.A.M., Foreman, J.C., Chain, B.M. (1994) The gold antirheumatic drug auranofin governs T cell activation by enhancing oxygen free radical production. European Journal of Immunology, vol. 24, p. 1961-1965.*
Li, L., Wang, C.C. (2006) A likely molecular basis of the susceptibility of *Giardia lamblia* towards oxygen. Molecular Microbiology, vol. 59, No. 1, p. 202-211.*
Byrd et al.; "*Giardia lamblia* Infections in Adult Mice"; Infection and Immunity; Aug. 1994; vol. 62 No. 8; p. 3583-3585.

(Continued)

*Primary Examiner* — Scarlett Goon
(74) *Attorney, Agent, or Firm* — Cantor Colburn LLP (57) ABSTRACT Compounds useful for the treatment of giardiasis are described.

1 Claim, 2 Drawing Sheets (56) References Cited

OTHER PUBLICATIONS

Nash et al.; "Antigenic Variation in *Giardia lamblia*"; The Journal of Immunology; Jul. 1988; vol. 141 No. 2; p. 636-641.
Keister; "Axenic Culture of Giardia Lambli in TYI-S-33 medium supplemented with Bile"; Transactions of the Royal Society of Tropical Medicine and Hygiene; 1983; vol. 77 No. 4; p. 487-488.
Zhang et al.; "A Simple Statistical Parameter for Use in Evaluation and Validation of High Throughput Screening Assays"; Journal of Biomolecular Screening; Apr. 1999; vol. 4 No. 2; p. 67-73.
Inglese et al.; "Quantitative High-Throughput Screening: A Titration-Based Approach that Efficiently Identifies Biological Activities in Large Chemical Libraries"; Proc. Natl. Acad. Sci. USA; Aug. 2006; p. 11473-11478.
Busatti et al; "The Old and New Therapeutic Approaches to the Treatment of Giardiasis: Where are We?"; Biologics: Targets & Therapy; 2009; vol. 3; p. 273-287.
Dunn et al.; "A New-Generation 5-Nitroimidazole Can Induce Highly Metronidazole-resistant *Giardia lamblia* In Vitro"; Int'l Journal of Antimicrobial Agengs; Jul. 2010; vol. 36 Issue 1; p. 37-42.
Valdez et al; "Synthesis and Electrochemistry of 2-Ethenyl and 2-Ethanyl Derivatives of 5-Nitroimidazole and Antimicrobial Activity against *Giardia lamblia*"; Journal of Medicinal Chemistry; vol. 52; May 2009; p. 4038-4053.
Mentasti et al.; "The Effect of Fumagillin in Intestinal Amoebiasis"; Ospedele Maggiore; 1955; vol. 43 No. 6; p. 201-205; Not in Engilsh.
Nash et al.; "Efficacies of Zinc-Finger-Active Drugs against *Giardia lamblia*"; Antimicrobial Agents and Chemotherapy; Jun. 1998; vol. 42 No. 6; p. 1488-1492.
Wilhelm et al.; "Urticaria Associated with *Giardiasis lamblia*"; Journal of Allergy; Jul. 1957; vol. 28 No. 4; p. 351-353.
International Patent Application No. PCT/US2011/055902; Int'l Search Report and the Written Opinion; dated Mar. 27, 2012; 15 pages.
Morgan et al.; "Activities of Several Benzimidazoles and Tubulin Inhibitors against *Giardia* spp. In Vitro"; Antimicrobiai Agents and Chemotherapy; Feb. 1993; vol. 37 No. 2; p. 328-331.
Mariante et al.; "*Giardia lamblia*: Evaluation of the in vitro effects of nocodazole and colchicine on trophozoites"; Experimental Parasitology; May 2005; vol. 110 Issue 1; p. 62-72.
International Patent Application No. PCT/US2011/055902; Int'l Preliminary Report on Patentability; dated Apr. 25, 2013; 9 pages.

\* cited by examiner

METHODS OF TREATING GIARDIASIS

CROSS REFERENCE TO RELATED APPLICATION

This application is the U.S. national stage application of PCT/US2011/055902 filed on Oct. 12, 2011, which claims the benefit of priority to U.S. Provisional Application No. 61/392,096 filed Oct. 12, 2010, and U.S. Provisional Application No. 61/411,509, filed Nov. 9, 2010, the disclosures of which are incorporated herein by reference in their entireties.

TECHNICAL FIELD

The invention is directed to compounds and methods for the treatment of giardiasis. Methods of identifying compounds that act against *Giardia lamblia* and that can be used for the treatment of giardiasis are also described.

BACKGROUND

The human pathogen *Giardia lamblia* is an anaerobic protozoan parasite that causes giardiasis, one of the most common diarrheal diseases worldwide. Although several drugs are available for the treatment of giardiasis, drug resistance has been reported and is likely to increase, and recurrent infections are common. Thus, identification of additional compounds useful for the treatment of giardiasis are needed.

SUMMARY

The invention is directed to methods of treating giardiasis. These methods include administering to a patient a therapeutically effective amount of a compound that is fumagillin, bortezomib, acivicin, nitarsone, decitabine, riboflavin butyrate, BTO-1, carbadox, GW9662, hydroxocobalamin, dinitroph-dfgp, deserpidine, amlexanox, tetramethylthiuram disulfide, disulfiram, vinblastine, idarubincin, mitoxantrone, auranofin, ecteinascidin 743, 17-allylamino geldanamycin, carboquone, nocodzole, CB1954, resveratrol, piceatannol, tioxidazole, tenonitrozol, nithiamide, nifuroxime, or diphenyleneiodonium chloride, or a pharmaceutically acceptable salt form thereof.

BRIEF DESCRIPTION OF THE DRAWINGS

FIG. 1 depicts assay development in 96-well format. (a) *G. lamblia* WB trophozoite samples were treated with 0.42% DMSO control or 41.7 µM metronidazole (Mnz) and were incubated anaerobically at 37° C. for indicated periods of time. RLU=relative luminescence unit. (b) DMSO tolerance of the growth assay was tested between 0.07% and 8.3% DMSO. (c) Dose response of Mnz on *Giardia* growth.

FIG. 2 depicts assay miniaturization to 1536-well format. (a) Dose-response curves for Metronidazole (Mnz) treatment on 3 plating densities of *Giardia*. Calculated EC50s are: 2.9 µM for 100 cells/well, 2.9 µM for 200 cells/well and 2.1 µM for 300 cells/well *Giardia* density. Percent total signal is calculated based on 32 wells each of DMSO (100%) and Mnz (0%) treatment for each of the cell densities. (b) Scatter plot for a DMSO test plate. Columns 1 and 2 were treated with Mnz titration, column 3 with 38.3 µM Mnz and columns 4-48 with 0.38% DMSO. RLU=relative luminescence unit. CV=coefficient of variation.

DETAILED DESCRIPTION OF ILLUSTRATIVE EMBODIMENTS

Compounds that exhibit anti-*Giardia* activity have been identified. As a result, the compounds of the invention will be useful in the treatment of giardiasis in humans and other mammals, for example, domestic animals such as cats and dogs.

In addition to the described compounds of the invention described as having anti-*Giardia* activity, appropriate pharmaceutically acceptable salts and free bases and free acids of the compounds are also envisioned.

Some compounds of the invention include one or more chiral centers and, as a result, compounds of the invention may have enantiomers or diastereomers. In addition to the compounds expressly set forth herein, all enantiomers and diastereomers are also fully envisioned to be within the scope of the invention.

Compounds that have been discovered to exhibit anti-*Giardia* activity useful in the treatment of giardiasis in humans and other mammals are fumagillin, bortezomib, acivicin, nitarsone, decitabine, riboflavin butyrate, BTO-1, carbadox, GW9662, hydroxocobalamin, dinitroph-dfgp, deserpidine, amlexanox, tetramethylthiuram disulfide, disulfiram, vinblastine, idarubincin, mitoxantrone, auranofin, ecteinascidin 743, 17-allylamino geldanamycin, carboquone, nocodzole, CB1954, resveratrol, piceatannol, tioxidazole, tenonitrozol, nithiamide, nifuroxime, or diphenyleneiodonium chloride, or a pharmaceutically acceptable salt form thereof.

In one embodiment, the compound useful in the treatment of giardiasis in humans and other mammals is fumagillin, bortezomib, acivicin, nitarsone, decitabine, riboflavin butyrate, BTO-1, carbadox, GW9662, hydroxocobalamin, dinitroph-dfgp, deserpidine, amlexanox, tetramethylthiuram disulfide, vinblastine, idarubincin, mitoxantrone, auranofin, ecteinascidin 743, 17-allylamino geldanamycin, carboquone, nocodzole, resveratrol, piceatannol, tioxidazole, tenonitrozol, nithiamide, nifuroxime, or diphenyleneiodonium chloride, or a pharmaceutically acceptable salt form thereof.

In preferred embodiments, the compound useful in the treatment of giardiasis in humans and other mammals is fumagillin, bortezomib, acivicin, nitarsone, decitabine, riboflavin butyrate, BTO-1, carbadox, GW9662, hydroxocobalamin, dinitroph-dfgp, deserpidine, amlexanox, tetramethylthiuram disulfide, disulfiram, idarubincin, mitoxantrone, auranofin, ecteinascidin 743, 17-allylamino geldanamycin, carboquone, nocodzole, CB1954, resveratrol, piceatannol, tioxidazole, tenonitrozol, nithiamide, or nifuroxime, or a pharmaceutically acceptable salt form thereof.

In other embodiments, the compound useful in the treatment of giardiasis in humans and other mammals is fumagillin, bortezomib, nitarsone, decitabine, carbadox, deserpidine, 17-allylamino geldanamycin, carboquone, nocodzole, piceatannol, tioxidazole, tenonitrozol, nithiamide, nifuroxime, or a pharmaceutically acceptable salt form thereof.

In still other embodiments, the compound useful in the treatment of giardiasis in humans and other mammals is fumagillin, bortezomib, decitabine, carbadox, nitarsone, BTO-1, GW9662, or hydroxocobalamin, or a pharmaceutically acceptable salt form thereof.

One preferred compound for use in the invention is fumagillin, or a pharmaceutically acceptable salt form thereof.

Another preferred compound for use in the invention is bortezomib, or a pharmaceutically acceptable salt form thereof.

Acivicin, or a pharmaceutically acceptable salt form thereof, is a preferred compound for use in the invention.

Nitarsone, or a pharmaceutically acceptable salt form thereof, is another preferred compound for use in the invention.

A preferred compound for use in the invention is decitabine, or a pharmaceutically acceptable salt form thereof.

Another preferred compound for use in the invention is riboflavin butyrate, or a pharmaceutically acceptable salt form thereof.

Still another preferred compound for use in the invention is BTO-1, or a pharmaceutically acceptable salt form thereof.

Yet another preferred compound for use in the invention is carbadox, or a pharmaceutically acceptable salt form thereof.

GW9662, or a pharmaceutically acceptable salt form thereof, is a preferred compound for use in the invention.

Hydroxocobalamin, or a pharmaceutically acceptable salt form thereof, is also a preferred compound for use in the invention.

Also preferred for use in the invention is dinitroph-dfgp, or a pharmaceutically acceptable salt form thereof.

Another preferred compound for use in the invention is deserpidine, or a pharmaceutically acceptable salt form thereof.

Still another preferred compound for use in the invention is amlexanox, or a pharmaceutically acceptable salt form thereof.

Yet another compound useful in the invention is tetramethylthiuram disulfide, or a pharmaceutically acceptable salt form thereof.

Another preferred compound for use in the invention is disulfiram, or a pharmaceutically acceptable salt form thereof.

Also preferred for use in the invention is vinblastine, or a pharmaceutically acceptable salt form thereof.

Idarubincin is also a preferred compound for use in the invention, or a pharmaceutically acceptable salt form thereof.

One preferred compound for use in the invention is mitoxantrone, or a pharmaceutically acceptable salt form thereof.

Another preferred compound for use in the invention is auranofin, or a pharmaceutically acceptable salt form thereof.

Yet another preferred compound for use in the invention is ecteinascidin 743, or a pharmaceutically acceptable salt form thereof.

Still another preferred compound for use in the invention is 17-allylamino geldanamycin, or a pharmaceutically acceptable salt form thereof.

Also preferred for use in the invention is carboquone, or a pharmaceutically acceptable salt form thereof.

Nocodzole, or a pharmaceutically acceptable salt form thereof, is another preferred compound of the invention.

CB1954, or a pharmaceutically acceptable salt form thereof, is also a preferred compound of the invention.

Resveratrol is also a preferred compound of the invention, or a pharmaceutically acceptable salt form thereof.

Another preferred compound of the invention is piceatannol, or a pharmaceutically acceptable salt form thereof.

Yet another preferred compound of the invention is tioxidazole, or a pharmaceutically acceptable salt form thereof.

Still another preferred compound of the invention is tenonitrozol, or a pharmaceutically acceptable salt form thereof.

Also preferred for use in the invention is nithiamide, or a pharmaceutically acceptable salt form thereof.

Another preferred compound for use in the invention is nifuroxime, or a pharmaceutically acceptable salt form thereof.

Yet another preferred compound for use in the invention is diphenyleneiodonium chloride, or a pharmaceutically acceptable salt form thereof.

Administration of mixtures of any of the foregoing compounds for the treatment of giardiasis is also within the scope of the invention.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenyl acetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

The compounds of the invention may be administered in an effective amount by any of the conventional techniques well-established in the medical field. The compounds may be administered by any conventional means available.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspensing/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, *acacia*, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

Materials and Methods

Materials

Mnz, 5-Aza-2'-deoxycytidine (decitabine), nitarsone, carbadox, GW9662 and hydroxocobalamin acetate were purchased from Sigma-Aldrich (Saint Louis, Mo.). Fumagillin was purchased from Enzo Life Sciences (Plymouth Meeting, Pa.), bortezomib, from Santa Cruz Biotechnology (Santa Cruz, Calif.), and BTO-1, from EMD Chemicals (Gibbstown, N.J.). All compounds were dissolved in DMSO to either 50 mM or 10 mM depending on solubility. The ATPLite 1 Step luminescence assay kit was purchased from PerkinElmer (Waltham, Mass.).

*Giardia* Culture

Trophozoites of the *G. lamblia* isolates WB and GS (Byrd, L. G., J. T. Conrad, and T. E. Nash. 1994. *Giardia lamblia* infections in adult mice. Infect Immun 62:3583-5; Nash, T. E., A. Aggarwal, R. D. Adam, J. T. Conrad, and J. W. Merritt, Jr. 1988. Antigenic variation in *Giardia lamblia*. J Immunol 141:636-41) were grown at pH 7.0 in modified TYI-S-33 medium as described previously (Keister, D. B. 1983. Axenic culture of *Giardia lamblia* in TYI-S-33 medium supplemented with bile. Trans R Soc Trop Med Hyg 77:487-8). The medium was supplemented with 10% heat inactivated bovine serum (Sigma) and 0.05% bovine bile (Sigma) in borosilicate glass screw-cap culture tubes (Fisherbrand). To attain low-oxygen tension conditions, the tubes were filled to 85-90% of their total volume capacity and incubated without shaking at 37° C. Subcultures (2×105 trophozoites per tube) were made three times a week. Detachment of trophozoites for preparation of inocula was achieved by chilling the cultures on ice for 20 min.

*Giardia* Viability Assay in 96-Well Format

*Giardia* trophozoites were plated at a density of 2500 cells/well in 120 µL media in sterile 96-well black clear-bottom assay plates. Mnz was serially diluted from 100 mM stock solution 1:4 in DMSO and then 0.5 µL/well of Mnz titrations or DMSO control were transferred in duplicates to the assay wells using a multichannel pipette. The assay plates were covered with plastic low-evaporation lids and individually sealed with anaerobic generators (Type A Bio-Bag, BD Diagnostics) to create anaerobic growth environment. The sealed Bio-Bags were incubated at 37° C. for indicated periods. Following incubation, 80 µL/well of the ATPLite reagent (PerkinElmer) was added to the assay plates for one-step lysis and ATP level detection. The plates were centrifuged briefly (1000 RPM, 30 seconds) and incubated at room temperature for 20 min. The luminescent signals of assay plates were measured on a ViewLux plate reader (PerkinElmer). Signal-to-basal (S/B) ratios and Z' factors were calculated from 8 wells containing 0.42% DMSO (total signal) and 8 wells containing 41.7 µM Mnz (basal signal).

*Giardia* Viability Assay in 1536-Well Format

For the viability assay in 1536-well format, 2 µL media was dispensed per well into 1536-well white solid-bottom plates using a Multidrop Combi dispenser (Thermo Scientific). Subsequently, 23 nL/well compound solutions or DMSO controls were dispensed to the assay plates containing media via a pintool workstation (Kalypsys, San Diego). Trophozoites were chilled on ice to detach from glass tubes, and unless otherwise noted, were diluted to 250,000 trophozoites/mL with ice cold media. The trophozoite suspension was kept on ice and dispensed as 4 µL/well with the Multidrop Combi dispenser. Attachment of trophozoites to dispensing apparatus was avoided with continuous dispensing and icing of the trophozoite suspension. The plates were covered with plastic low-evaporation lids, individually sealed in Type A Bio-Bags and incubated at 37° C. for 48 hours. Following incubation, 4 µL/well of ATPLite reagent was dispensed with the Multidrop Combi dispenser. The assay plates were briefly centrifuged at 1000 RPM and luminescence signal was detected on a ViewLux plate reader (PerkinElmer) after 20 min incubation at room temperature. Signal-to-basal (S/B) ratio, Z' factor and coefficient of variation (CV) were calculated from 32 wells with 0.38% DMSO (total signal) and 32 well with 38.3 µM Mnz (basal signal).

CHO Cell Cytotoxicity Assay in 1536-Well Format

For the viability assay in 1536-well format, 2 µL media was dispensed per well into 1536-well white solid-bottom plates using Multidrop Combi dispenser. Subsequently, 23 nL/well compound solutions or DMSO controls were dispensed to the assay plates via a pintool workstation. The Chinese hamster ovary (CHO) cells were grown in T225 flasks to 70% confluence under a standard cell culture condition (ATCC), detached with 0.25% Trypsin/EDTA, and seeded at 250 cells/well in 4 µL media (Dulbecco's Modified Eagle Medium, 10% fetal bovine serum, 1× penicillin/streptomycin). The plates were incubated at 37° C. with 5% $CO_2$ and 95% humidity for 48 hours. Subsequently, ATP content was measured following the addition of 4 µL/well of ATPLite reagent and a 20 min incubation on a ViewLux plate reader.

Trophozoite Enumeration Assay

*Giardia lamblia* GS isolate was plated into sterile 96-well black clear-bottom assay plates at 10,000 cells/well density and 120 µL/well volume in culture media. Compounds tested were prepared as 50 mM DMSO solutions in a 12 point 1:3 titration series in DMSO, with exceptions being carbadox, Bortezomib and BTO-1, which were used at 10 mM top concentration due to solubility limitations. Compound titration series were added to duplicate assay wells as 0.5 µL/well and the assay plates were incubated anaerobically in Type A Bio-Bag (BD Diagnostics) for 48 hrs at 37° C. Cell density was visually scored in each well and the 6 wells surrounding the visually determined $IC_{50}$ concentrations were quantitated by cell counting. For enumeration, trophozoites were detached on ice for 30 min and resuspended via pipetting. 75 µL of culture was removed from each well, mixed with 65 µL of 0.4% Trypan Blue and 10 µL of 30% bleach (final concentration of 2% bleach) to immobilize trophozoites. Trophozoites were then counted in a hemocytometer.

Data Analysis

Statistical values for assay robustness were calculated as follows:

Z' factor=1−3 $(SD_{Total}+SD_{Basal})/(Mean_{Total}-Mean_{Basal})$, where $SD_{Total}$ is the standard deviation of DMSO treated wells, $SD_{Basal}$ is the standard deviation of Mnz treated wells, $Mean_{Total}$ is the mean of DMSO treated wells and $Mean_{Basal}$ is the mean of Mnz treated wells (Zhang, J. H., T. D. Chung, and K. R. Oldenburg. 1999. A Simple Statistical Parameter for Use in Evaluation and Validation of High Throughput Screening Assays. J Biomol Screen 4:67-73).

Coefficient of variation (CV)=$SD_{Total}/Mean_{Basal}$, expressed as a percentage.

Data normalization and curve fitting was performed as previously described (Inglese, J., D. S. Auld, A. Jadhav, R. L. Johnson, A. Simeonov, A. Yasgar, W. Zheng, and C. P. Austin. 2006. Quantitative high-throughput screening: a titration-based approach that efficiently identifies biological activities in large chemical libraries. Proc Natl Acad Sci USA 103: 11473-8.).

Data from the CHO cell counter-screen underwent the same initial analysis, with the exception that raw luminescence counts were normalized relative to DMSO only wells (0% activity) and 38.3 µM camptothecin treated wells (100% activity). For evaluation of cytotoxicity, compounds that were at least 10-fold less potent (IC50 over 10-fold higher) or 50% less efficacious (maximal response less than 50%) in the CHO cell assay compared with respective values in the *Giardia* assay were considered selective anti-*Giardia* compounds.

Results

ATP Content Assay Development

Figure 1A:
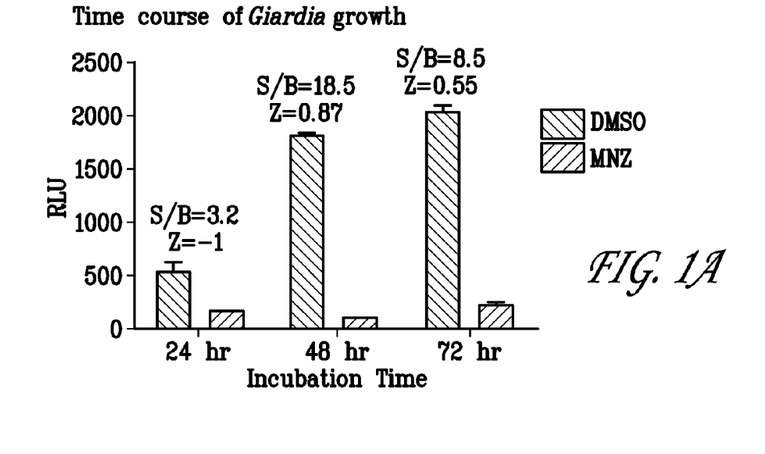
Figure 1B:
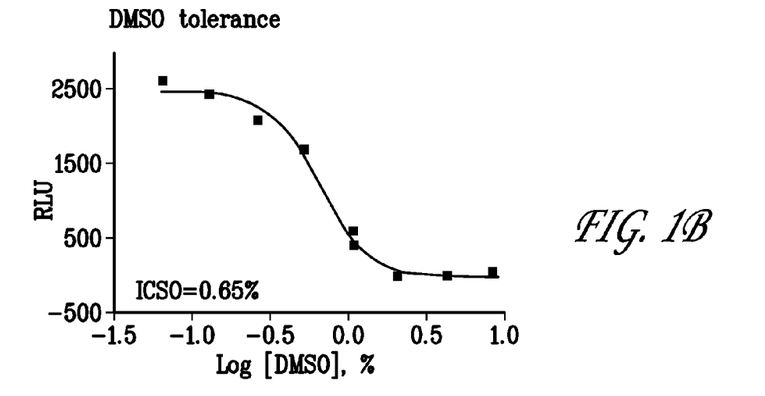

A commercially available ATP detection kit to measure the viability of *G. lamblia* after compound treatment. This bioluminescence assay utilizes the luciferase enzyme reaction with two substrates, luciferin and the ATP derived from the live cell lysate, to produce light. The assay was developed in 96-well plate format and the known giardiacidal agent Mnz was used as a positive control (Busatti, H. G., J. F. Santos, and M. A. Gomes. 2009. The old and new therapeutic approaches to the treatment of giardiasis: Where are we? Biologics 3:273-87). The time course of *Giardia* WB clone growth showed an increase in ATP signal up to 48 hrs and reaching a plateau between 48 and 72 hrs (FIG. 1*a*). Based on these growth characteristics, the 48 hr time point was selected for compound treatments. At all time points tested, 41.7 µM Mnz treatment reduced the ATP content to <5% of the DMSO control values (FIG. 1*a*). The DMSO tolerance of trophozoites was assessed in this assay as DMSO is used to dissolve the compounds in the library. DMSO suppressed the assay signal in a concentration dependent manner. At the 0.38% DMSO concentration, which was used for the compound screening, there was a 20-30% reduction in the ATP signal (FIG. 1*b*).

Figure 1C:
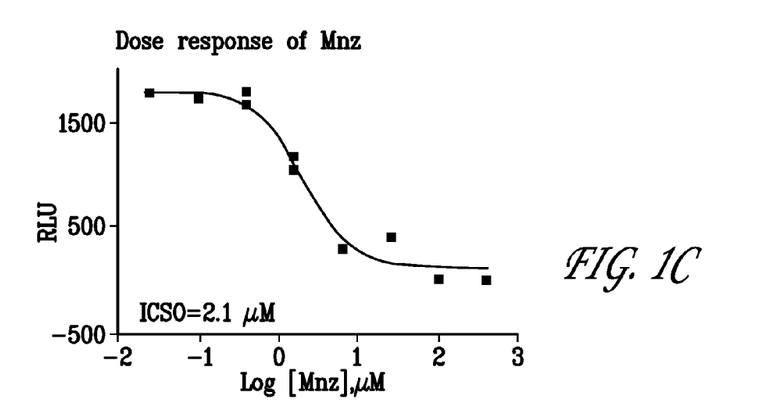

Mnz, the giardiacidal control compound, showed a concentration dependent inhibition of the ATP content signal with an $IC_{50}$ value of 2.1 μM (FIG. 1c), which agrees with previously reported values (Dunn, L. A., et al. 2010. A new generation 5-nitroimidazole can induce highly metronidazole-resistant *Giardia lamblia* in vitro. *Int J Antimicrob Agents* 36:37-42. Valdez, C. A., et al. 2009. Synthesis and electrochemistry of 2-ethanyl derivatives of 5-nitroimidazole and antimicrobial activity against *Giardia lamblia*. *J Med Chem* 52:4038-53).

Miniaturization of the ATP Content Assay

Figure 2A:
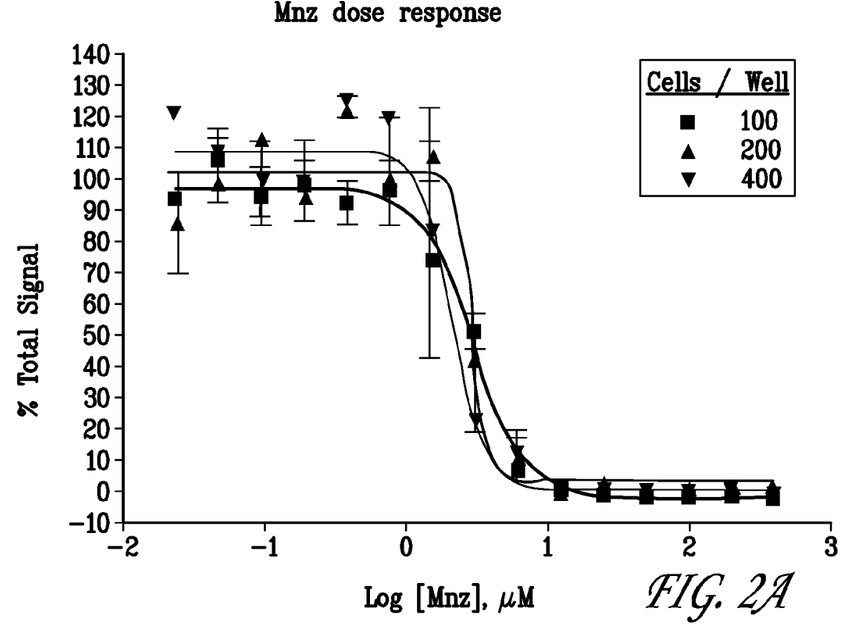
Figure 2B:
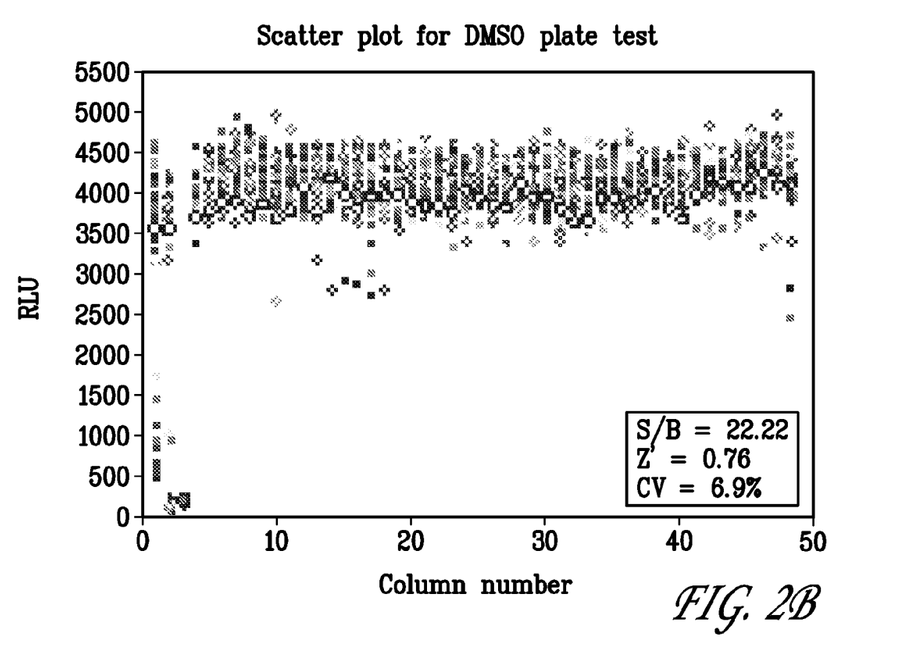

Assay miniaturization in 1,536-well plate format was undertaken to increase throughput and facilitate screening of large compound libraries. The volume of trophozoites suspension was reduced to 6 μL/well and the ATP detection reagent was reduced to 4 μL/well in the 1536-well assay plates. The assay was tested at 3 different trophozoites densities of 100, 200 and 400 trophozoites/well to determine the activity of Mnz. All three cell densities showed similar sensitivity towards Mnz with comparable $IC_{50}$ values that also matched the results from the 96-well format assay (FIG. 2a), indicating that the miniaturization retained assay sensitivity and robustness. The 100 trophozoites/well density was selected for further experiments to reduce the preparation work of *Giardia* cultures. Following these conditions, a DMSO test plate was used to assess the statistical parameters of the assay in the 1,536-well plate format. The S/B, Z' factor and CV values were 22.2, 0.76 and 6.9%, respectively (FIG. 2b), indicating that the miniaturized assay is robust and suitable for HTS.

Compound Library Screen and Hit Confirmation

Using the above established conditions in 1536-well format, each compound of the invention was tested at 5 concentration points, ranging from 61 nM-38.3 μM in a 1:5 dilution ratio (Inglese, J., D. S. Auld, A. Jadhav, R. L. Johnson, A. Simeonov, A. Yasgar, W. Zheng, and C. P. Austin. 2006. Quantitative high-throughput screening: a titration-based approach that efficiently identifies biological activities in large chemical libraries. Proc Natl Acad Sci USA 103:11473-8).

In order to assess the specificity of the confirmed hits towards *Giardia* and to eliminate false positives such as luciferase inhibitors, a counter-screen was developed using the CHO cells with the same ATP content assay. CHO cells, commonly used in high throughput compound screening, were selected to determine the cytotoxicity of the compounds towards a mammalian cell line. When the compounds of the invention were incubated with CHO cells for 48 hr and the cytotoxicity was detected by the ATP content assay, compounds were found to be selective towards *Giardia*. Selective anti-*Giardia* compounds found in the screen are listed in Table 1 and Table 2.

TABLE 1

| Comp. Name | Structure | Giardia WB | | CHO | |
| --- | --- | --- | --- | --- | --- |
| | | $IC_{50}$ (μM)[1] | Efficacy (%)[2] | $IC_{50}$ (μM)[1] | Efficacy (%)[3] |
| Fumagillin | | 0.01 | 83.4 | >100 | −1.9 |
| Bortezomib (S,S) | | 0.11 | 94.4 | 0.02 | 48.2 |
| Bortezomib (S,R) | | 0.07 | 92.8 | 0.01 | 36.2 |

TABLE 1-continued

| Comp. Name | Structure | Giardia WB | | CHO | |
|---|---|---|---|---|---|
| | | $IC_{50}$ ($\mu M$)[1] | Efficacy (%)[2] | $IC_{50}$ ($\mu M$)[1] | Efficacy (%)[3] |
| Acivicin | | 0.17 | 85.9 | 27.37 | 52.5 |
| Nitarsone | | 0.43 | 97.0 | >100 | −13.5 |
| Decitabine | | 0.97 | 81.2 | 24.39 | −52.2 |
| Riboflavin Butyrate | | 1.09 | 95.7 | >100 | 20.3 |
| BTO-1 | | 1.73 | 72.3 | 68.75 | 32.2 |
| Carbadox | | 5.46 | 86.6 | >100 | 6.3 |

TABLE 1-continued

| Comp. Name | Structure | Giardia WB IC$_{50}$ (μM)[1] | Efficacy (%)[2] | CHO IC$_{50}$ (μM)[1] | Efficacy (%)[3] |
|---|---|---|---|---|---|
| GW9662 | | 6.87 | 86.4 | >100 | 8.5 |
| Hydroxocobalamin Acetate | | 13.72 | 92.2 | >100 | 16.1 |
| Dinitroph-dfgp | | 43.38 | 44.2 | >100 | −8.0 |
| Deserpidine | | 1.63 | 94.5 | 0.28 | 13.0 |

TABLE 1-continued

| Comp. Name | Structure | Giardia WB IC$_{50}$ (μM)[1] | Giardia WB Efficacy (%)[2] | CHO IC$_{50}$ (μM)[1] | CHO Efficacy (%)[3] |
|---|---|---|---|---|---|
| Amlexanox | | 2.59 | 92.4 | 3.26 | 89.3 |
| Tetramethylthiuram disulfide | | 5.16 | 97.6 | 0.52 | 97.6 |
| Disulfiram | | 6.50 | 95.0 | 0.2 | 53.6 |
| Vinblastine sulfate | | 1.45 | 90.1 | 0.1 | 64.1 |
| Idarubicin HCl | | 3.26 | 94.1 | 0.2 | 88.7 |
| Mitoxantrone | | 8.19 | 87.5 | 5.8 | 95.8 |

TABLE 1-continued

| Comp. Name | Structure | Giardia WB IC$_{50}$ (μM)[1] | Giardia WB Efficacy (%)[2] | CHO IC$_{50}$ (μM)[1] | CHO Efficacy (%)[3] |
|---|---|---|---|---|---|
| Auranofin | | 8.19 | 97.1 | 11.57 | 97.5 |
| Ecteinascidin 743 | | 0.00651 | 95.9 | 0.05 | 97.6 |
| 17-Allylamino geldanamycin | | 0.0819 | 95.6 | 0.52 | 86.9 |
| Carboquone | | 0.1834 | 97.4 | 0.58 | 98.4 |
| Nocodazole | | 0.1834 | 86.7 | 0.37 | 54.4 |

TABLE 1-continued

| Comp. Name | Structure | Giardia WB | | CHO | |
|---|---|---|---|---|---|
| | | IC$_{50}$ (μM)[1] | Efficacy (%)[2] | IC$_{50}$ (μM)[1] | Efficacy (%)[3] |
| Diphenylene-iodonium chloride |  | 0.259 | 96.0 | 2.06 | 95.9 |
| Parbendazole |  | 0.3117 | 90.2 | 0.44 | 60.3 |
| CB 1954 |  | 0.12 | 96.4 | >100 | −16.9 |
| Resveratrol |  | 4.94 | 80.7 | 39.24 | 22.2 |
| Piceatannol |  | 3.26 | 81.3 | >100 | −16.6 |
| Tioxidazole |  | 1.46 | 90.9 | >100 | 34.9 |
| Tenonitrozol |  | 0.29 | 93.1 | >100 | 21.5 |
| Nithiamide |  | 0.58 | 94.6 | >100 | 25.9 |

TABLE 1-continued

| Comp. Name | Structure | Giardia WB IC$_{50}$ (μM)[1] | Giardia WB Efficacy (%)[2] | CHO IC$_{50}$ (μM)[1] | CHO Efficacy (%)[3] |
|---|---|---|---|---|---|
| Nifuroxime | [structure] | 0.46 | 97.1 | 41.05 | −50.3 |

[1]IC$_{50}$ was calculated as the conventration of compound at which 50% of DMSO control ATP levels are detected.
[2]Efficacy was normalized to percent reduction in ATP levels compared with 38.3 mM Mnz at maximal compound concentration.
[3]Efficacy normalized to percent reduction in ATP levels compared with 38.3 mM camptothecin at maximal compound concentration.

TABLE 2

| Comp. Name | Giardia GS IC$_{50}$ (μm) |
|---|---|
| Fumagillin | 0.002 |
| Decitabine | 0.100 |
| Deserpidine | 0.283 |
| Riboflavin Butyrate | 1.127 |
| Nithiamide | 0.317 |
| Nifuroxime | 1.004 |
| Tioxidazole | 0.634 |
| Carbadox | 2.831 |
| Piceatannol | 3.564 |
| Nitarsone | 1.264 |

As a further confirmatory step, some compounds that were commercially available were purchased as powder samples and tested against the *G. lamblia* GS isolate using both the ATP content and enumeration assays (Table 3).

TABLE 3

| | ATP Content | | Enumeration |
|---|---|---|---|
| Comp. Name | IC$_{50}$ (μM) | Efficacy (%) | IC$_{50}$ (μM) |
| Metronidazole | 1.6 | 99.7 | 2.2 |
| Fumagillin | 0.002 | 98.9 | 0.003 |
| Bortezomib | 0.06 | 98.5 | 0.13 |
| Decitabine | 0.15 | 95.1 | 0.07 |
| Carbadox | 0.24 | 99.4 | 0.29 |
| Nitarsone | 0.9 | 99.6 | 1.2 |
| BTO-1 | 2.0 | 99.1 | 9.3 |
| GW9662 | 12.7 | 99.2 | 32.9 |
| Hydroxocobalamin Acetate | 78.3 | 98.4 | 54.2 |

Minimum Lethal Concentration (MLC) Determination.

*Giardia lamblia* GS isolate was used throughout the Minimal Lethal Concentration (MLC) experiments. Organisms were grown and maintained in TYI-S-33 medium supplemented with bile and antibiotics (Keister, 1983). Cidal activity was determined in 96-well culture plates (Corning Incorporated) followed by *Giardia* trophozoites regrowth in 8 ml tubes (Fisher Scientific). Dry compounds were dissolved in DMSO (Sigma) at stock concentration of 10 mM and then added to the growth media to ensure final DMSO concentration of no more than 0.5%. 100 μl of the compound solutions were placed in the wells by serial dilutions. 10 μl of *Giardia* trophozoites containing 10000 organisms were then added. Serial dilutions of metronidazole served as the positive control and the DMSO-containing medium served as the negative control. Plates were incubated under anaerobic conditions in sealed bags (Becton Dickinson and Company) at 37° C. for 3 days and surveyed visually under microscope to check survival, mobility and attachment of trophozoites. The plate was chilled on ice for 30 min and the entire contents of 4 wells in the growth/death transition were transferred into the 8 ml tubes containing growth media only (without the compound). After 3 days of incubation at 37° C., tubes were checked under microscope for any surviving trophozoites. MLC was attributed to the tube without any live organisms. The results of these experiments are set forth in Table 4. See, e.g., Keister, D. B. 1983. Axenic culture of *Giardia lamblia* in TYI-S-33 medium supplemented with bile. Trans. Soc. Trop. Med. Hyg. 77:487-488.

TABLE 4

| Compound | MLC* (μM) |
|---|---|
| corbadox | 4.6 |
| B12 (hydroxycobalamine) | >208 |
| bortezomib | 0.51 |
| nitarsone | 2.6 |
| GW9662 | 208 |
| decitabine | 2.6 |
| fumagillin | 0.257 |
| resveratrol | >208 |
| MNZ (metronidazole) | 7.7 |
| 17-Allyl amino geldanamycin | 13.9 |
| Nocodazole | 0.15 |
| Tenonitrozole | 1.54 |
| Auranofin | 41.7 |
| Idarubicin | >41.7 |
| Mitoxantrone | >41.7 |
| Amlexanox | >41.7 |
| Tioxidazole | 1.54 |
| Nifuroxime | 1.54 |
| Nithiamide | 4.63 |
| Carboquone | 1.54 |
| Riboflavin butyrate | 41.7 |
| Deserpidine | 1.54 |
| Piceatannol | 13.9 |

What is claimed:

1. A method of treating giardiasis in a patient having said condition, comprising administering to the patient a therapeutically effective amount of auranofin or a pharmaceutically acceptable salt form thereof.

* * * * *